US012788277B2

(12) United States Patent
Ghosh et al.

(10) Patent No.: US 12,788,277 B2
(45) Date of Patent: Nov. 10, 2026

(54) METHOD AND SYSTEM FOR ASSESSING CARDIORESPIRATORY HEALTH

(71) Applicant: TURTLE SHELL TECHNOLOGIES PRIVATE LIMITED, Bengaluru (IN)

(72) Inventors: Abin Ghosh, Bengaluru (IN); Mudit Dandwate, Bengaluru (IN); Gaurav Parchani, Bengaluru (IN)

(73) Assignee: TURTLE SHELL TECHNOLOGIES PRIVATE LIMITED, Bengaluru (IN)

( * ) Notice: Subject to any disclaimer, the term of this patent is extended or adjusted under 35 U.S.C. 154(b) by 0 days.

(21) Appl. No.: 19/381,494

(22) Filed: Nov. 6, 2025

(65) Prior Publication Data

US 2026/0108173 A1 Apr. 23, 2026

(30) Foreign Application Priority Data

Jun. 19, 2025 (IN) ............................ 202541059084

(51) Int. Cl.
*A61B 5/11* (2006.01)
*A61B 5/00* (2006.01)
(Continued)

(52) U.S. Cl.
CPC .......... *A61B 5/1102* (2013.01); *A61B 5/0803* (2013.01); *A61B 5/113* (2013.01); *A61B 5/4519* (2013.01); *A61B 5/4818* (2013.01); *A61B 5/6891* (2013.01); *A61B 5/7207* (2013.01); *A61B 5/7225* (2013.01); *A61B 5/7246* (2013.01); *A61B 5/725* (2013.01);
(Continued)

(58) Field of Classification Search
CPC ..... A61B 5/1102; A61B 5/0803; A61B 5/113; A61B 5/4519; A61B 5/4818; A61B 5/6891; A61B 5/7207; A61B 5/7225; A61B 5/7246; A61B 5/725; A61B 5/7257; A61B 5/726; A61B 5/7267; A61B 5/7271; A61B 5/746; A61B 2562/046
See application file for complete search history.

(56) References Cited

U.S. PATENT DOCUMENTS 10,426,380 B2 10/2019 Schindhelm et al.
11,679,217 B2 6/2023 Eweje et al.
2026/0047767 A1 * 2/2026 Ghosh .................. A61B 5/0205

* cited by examiner

*Primary Examiner* — Brian T Gedeon
(74) *Attorney, Agent, or Firm* — Maschoff Brennan

(57) ABSTRACT

The present disclosure provides a method for assessing cardiorespiratory health. The method comprising: generating mechanical movement data associated with a torso of a subject's body using a plurality of ballistocardiography (BCG) sensors; filtering the mechanical movement data to extract respiratory signal waveforms and heart signal waveforms; decomposing the respiratory signal waveforms into thoracic, diaphragmatic, and abdominal breathing components based on waveform characteristics and anatomical location of the plurality of BCG sensors; analyzing phase differences between the thoracic, diaphragmatic, and abdominal breathing components over time to quantify a degree of synchrony or asynchrony; evaluating relative contributions of thoracic, diaphragmatic, and abdominal breathing components to an overall breathing effort; identifying a breathing abnormality based on the analysed phase differences and the evaluated relative contributions; and detecting a potential cardiorespiratory condition based on the identified breathing abnormality.

20 Claims, 3 Drawing Sheets

(51) Int. Cl.
*A61B 5/08* (2006.01)
*A61B 5/113* (2006.01)

(52) U.S. Cl.
CPC ............ *A61B 5/7257* (2013.01); *A61B 5/726* (2013.01); *A61B 5/7267* (2013.01); *A61B 5/7271* (2013.01); *A61B 5/746* (2013.01); *A61B 2562/046* (2013.01)

METHOD AND SYSTEM FOR ASSESSING CARDIORESPIRATORY HEALTH

PRIORITY INFORMATION

The present application claims priority from Indian Patent Application Number 202541059084 filed on 19 Jun. 2025.

FIELD OF THE INVENTION

The present disclosure relates to a method for assessing cardiorespiratory health. The present disclosure also relates to a system for assessing cardiorespiratory health.

BACKGROUND OF THE INVENTION

Cardiorespiratory health is key indicator of overall well-being, with conditions such as chronic obstructive pulmonary disease (COPD), sleep apnoea, respiratory muscle fatigue, and diaphragmatic dysfunction significantly impacting quality of life. The conditions are often associated with breathing irregularities, including thoracoabdominal asynchrony and imbalances in breathing effort distribution, which can serve as early indicators of underlying pathophysiology. Early detection and continuous monitoring of these abnormalities are essential for timely intervention and effective disease management.

Existing solutions for assessing cardiorespiratory health rely on spirometry, polysomnography (PSG), or wearable pulse oximeters. While spirometry provides lung function data, it requires active patient participation and is unsuitable for continuous monitoring. Moreover, the PSG is cumbersome, expensive, and typically confined to clinical settings. Wearable devices such as pulse oximeters and respiratory inductance plethysmography (RIP) belts require direct contact with skin of user, which may cause discomfort and compromise long-term adherence.

Therefore, in the light of foregoing discussion, there exists a need to overcome the aforementioned drawbacks.

SUMMARY OF THE INVENTION

A primary objective of the present disclosure seeks to provide a method for assessing cardiorespiratory health that provides a reliable and accurate analysis of contributions of different breathing movements for example, thoracic, diaphragmatic, and abdominal using plurality of ballistocardiography (BCG) sensos or non-contact sensors to determine abnormality in the breathing of a subject. Moreover, such determination of abnormality in the breathing aids in detection of a potential cardiorespiratory condition. Another objective of the present disclosure seeks to provide a system for assessing cardiorespiratory health using the aforementioned method. An aim of the present disclosure is to provide a solution that overcomes at least partially the problems encountered in prior art.

In a first aspect, an embodiment of the present disclosure provides a method for assessing cardiorespiratory health, the method comprising:

generating mechanical movement data associated with a torso of a subject's body using a plurality of ballistocardiography (BCG) sensors;

filtering the mechanical movement data to extract respiratory signal waveforms and heart signal waveforms;

decomposing the respiratory signal waveforms into thoracic, diaphragmatic, and abdominal breathing components based on waveform characteristics and anatomical location of the plurality of BCG sensors;

analyzing phase differences between the thoracic, diaphragmatic, and abdominal breathing components over time to quantify a degree of synchrony or asynchrony;

evaluating relative contributions of thoracic, diaphragmatic, and abdominal breathing components to an overall breathing effort;

identifying a breathing abnormality based on the analysed phase differences and the evaluated relative contributions; and detecting a potential cardiorespiratory condition based on the identified breathing abnormality.

In a second aspect, an embodiment of the present disclosure provides a system for assessing cardiorespiratory health, the system comprising:

a plurality of ballistocardiography (BCG) sensors configured to measure mechanical forces caused by breathing movements associated with a torso of a subject; and a processor operatively connected to the plurality of BCG sensors to generate mechanical movement data from the measured mechanical forces, wherein the processor is configured to:

filter the mechanical movement data to extract respiratory signal waveforms and heart signal waveforms;

decompose the respiratory signal waveforms into thoracic, diaphragmatic, and abdominal breathing components based on waveform characteristics and anatomical location of the plurality of BCG sensors;

analyse phase differences between the thoracic, diaphragmatic, and abdominal breathing components over time to quantify a degree of synchrony or asynchrony;

evaluate relative contributions of thoracic, diaphragmatic, and abdominal breathing components to an overall breathing effort;

identify breathing abnormality based on the analysed phase differences and the evaluating relative contributions; and detect a potential cardiorespiratory condition based on the identified breathing abnormality.

The aforementioned method and system are implanted to assess cardiorespiratory health using plurality of non-contact such as, ballistocardiography (BCG) sensors, minimizing any contact or an injection to skin of a subject (e.g., a person or a patient), eliminating a need for wearable devices or invasive procedures, thereby enhancing user comfort and compliance during continuous and remote monitoring. Moreover, the aforementioned method and the system further utilizes mechanical movement data from the plurality of BCG sensors to extract respiratory signal waveforms and heart signal waveforms, ensuring accurate assessment of the cardiorespiratory health without disrupting the subject's natural state. Moreover, the aforementioned method allows accurate analysis of phase and morphology of the respiratory signal waveforms and the heart signal waveforms thereby improving quality of assessment of cardiorespiratory health. Advantageously, the aforementioned system is configured to analyze phase differences between thoracic, diaphragmatic, and abdominal breathing components and evaluates their relative contributions to the overall breathing effort, allowing for precise detection of respiratory abnormalities. The integration of blind source separation techniques ensures accurate decomposition of breathing waveforms, leading to enhanced diagnosis of potential cardiorespiratory conditions while maintaining a seamless and unobtrusive monitoring experience.

Embodiments of the present disclosure substantially eliminate or at least partially address the aforementioned problems in the prior art, and facilitate assessment of cardiorespiratory health, thereby identifying breathing abnormality for detection of potential cardiorespiratory condition.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of embodiments, is better understood when read in conjunction with the appended drawings. For the purpose of illustrating the present disclosure, exemplary constructions of the disclosure are shown in the drawings. However, the present disclosure is not limited to specific instrumentalities disclosed herein. Moreover, those skilled in the art will understand that the drawings are not to scale.

Embodiments of the present disclosure will now be described, by way of example only, with reference to the following diagrams wherein.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

Figure 1:
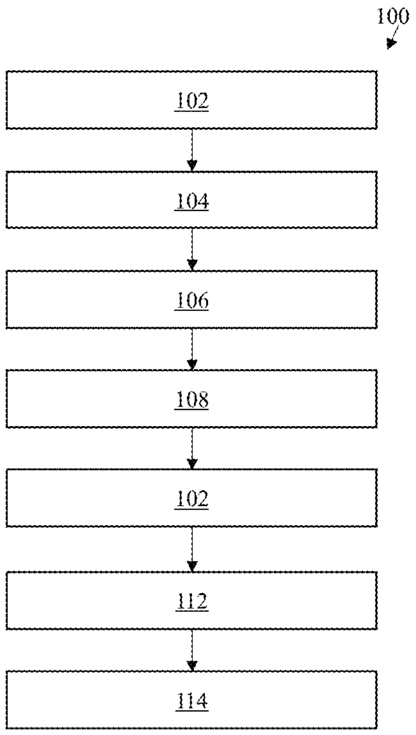
FIG. 1 illustrates a flowchart depicting steps of a method for assessing cardiorespiratory health, in accordance with an embodiment of the present disclosure.

Referring to FIG. 1, illustrated is a flowchart depicting steps of a method for assessing cardiorespiratory health, in accordance with an embodiment of the present disclosure. In this regard, throughout the present disclosure the term "cardiorespiratory health" refers to physiological state of a subject that reflects integrated function of both cardiovascular and respiratory systems. Notably, the cardiorespiratory health of the subject can be assessed in terms of various parameters including but not limited to heart rate variability, respiration rate, thoracoabdominal synchrony, cardiac output, oxygenation levels and the likes. It may be appreciated that the cardiorespiratory health is indicative of an ability of subject's body of the subject to transport oxygen efficiently and maintain stable circulatory and pulmonary function under varying physiological conditions. Herein, the term "subject" refers to a patient, a person, an animal, who's cardiorespiratory health may be assessed. Notably, the subject may reside in their home, old-age care institute, in a clinical setting such as in a hospital, a nursing home, a clinical research institute and so on. In this context, as shown in FIG. 1, at step 102, mechanical movement data associated with a torso of a subject's body is generated using a plurality of ballistocardiography (BCG) sensors. At step 104, the mechanical movement data is filtered to extract respiratory signal waveforms and heart signal waveforms. At step 106108, phase differences between the thoracic, diaphragmatic, and abdominal breathing components are analysed over time to quantify a degree of synchrony or asynchrony. At step 110, relative contributions of thoracic, diaphragmatic, and abdominal breathing components to an overall breathing effort are evaluated. At step 112, a breathing abnormality, the respiratory signal waveforms are decomposed into thoracic, diaphragmatic, and abdominal breathing components based on waveform characteristics and anatomical location of the plurality of BCG sensors. At step based on the analysed phase differences and the evaluated relative contributions is identified. At step 114, a potential cardiorespiratory condition is detected, based on the identified breathing abnormality.

Throughout the present disclosure, the term "mechanical movement data" refers to data representing mechanical movements such as, physical displacements, oscillations, or vibrations of the subject's body that arise due to physiological processes such as cardiac activity and respiratory movements. The mechanical movements result from internal biomechanical forces exerted by the heart and lungs (for example, vibrations/expansion-contraction movements observed during pumping of blood, or inhaling and exhaling air), which propagate as low-amplitude forces through the body's musculoskeletal system and can be detected using suitable sensors, namely, the plurality of BCG sensors. It may be appreciated that such mechanical movements captured by the plurality of BCG sensors are generated as the mechanical movement data. In this regard, "plurality ballistocardiogram (BCG) sensors" refers to non-invasive sensors configured to detect minute mechanical vibrations and displacement of the subject's body caused by cardiac ejection forces, blood flow dynamics, and respiratory motion. The plurality of BCG sensors captures mechanical forces generated by heartbeat and breathing cycles, enabling extraction of biomechanical and hemodynamic parameters for cardiorespiratory health assessment. The plurality of BCG sensors may include (not limited to) force-sensitive resistors, accelerometers, piezoelectric sensors, strain gauges, or pressure-sensitive transducers, which are strategically positioned to capture high-fidelity signals without direct contact with skin and/or the body of the subject.

It may be appreciated that the mechanical movement data (which is collected or obtained from the plurality of BCG sensors) is represented as waveforms comprising heart signal waveforms and respiratory signal waveforms. Throughout the present disclosure, the term "respiratory signal waveforms" refers to waveform components of the mechanical movement data which corresponds to movement observed in the subject's body due to respiratory functions such as inhalation and exhalation. It may be appreciated that the respiratory signal waveforms corresponds to rhythmic expansion and contraction of thoracic and abdominal cavities due to breathing Throughout the present disclosure, the term “heart signal waveforms” refers to waveform components of the mechanical movement data which corresponds to movement observed in the subject’s body due to cardiovascular functions and primarily results from the mechanical action of the heart of the subject such as the ejection of blood during systole, valve closure events, and recoil forces generated by circulatory dynamics.

In an embodiment, generating mechanical movement data comprises:

capturing analog signals associated with mechanical force caused by breathing movements using the plurality of BCG sensors;

amplifying the captured analog signals using low-noise amplifiers; and digitizing the amplified analog signals using analog-to-digital converters (ADCs) to generate the mechanical movement data.

In this regard, the term “breathing movements” used herein refers to a periodic expansion and contraction of body of the subject (specifically, the periodic expansion and contraction of thoracic, diaphragmatic and abdominal regions of the body) due to the inhalation and exhalation of air. The breathing movements create subtle mechanical force that propagate through the subject’s body and can be detected as vibrational signals by the plurality of BCG sensors. These breathing-induced forces result from diaphragmatic motion, rib cage expansion, and airway pressure changes, which collectively influence the mechanical forces recorded by the plurality of BCG sensors. Notably, the breathing movements encompass various respiratory patterns, including normal breathing, deep breathing, and irregular breathing patterns that may be indicative of conditions such as obstructive sleep apnoea, chronic obstructive pulmonary disease (COPD), or respiratory distress syndrome (RDS).

It may be appreciated that the plurality of BCG sensors captures the mechanical force which is generated by the breathing movements as the analog signals. However, the analog signals captured by the plurality of BCG are typically weak and susceptible to noise. Accordingly, the captured analog signals are amplified using low-noise amplifiers (LNAs) to enhance signal quality while minimizing electrical interference and unwanted signal distortions. The term “low-noise amplifiers” refers to specialized electronic circuits configured to increase an amplitude of weak analog signals while preserving their original characteristics with minimal introduction of additional noise. The LNAs ensure that the components of the analog signals (namely, the heart signal waveforms and the respiratory signal waveforms) remain distinguishable, thereby enabling accurate downstream analysis. For example, for a subject under sedation, where respiratory effort may be diminished, low-noise amplification ensures that even subtle mechanical oscillations are captured accurately.

Subsequently, the amplified analog signals are digitized using analog-to-digital converters (ADCs) to generate the mechanical movement data. The term “analog-to-digital converters” refers to electronic components that transform continuous-time analog signals into discrete digital representations by sampling the analog signal at predefined intervals. The ADCs facilitate numerical processing of the analog signals by converting real-world mechanical vibrations into structured digital data that can be subjected to filtering, feature extraction, and further computational analysis. The mechanical movement data, thus generated, comprises digitized representations of bodily micro-movements associated with respiratory cycles. Such data forms the basis for deriving key respiratory parameters, including breathing rate, breathing depth, and respiratory effort. By converting the raw mechanical signals into a digital format, precise and reliable monitoring of respiratory mechanics is ensured, enabling assessment of a subject’s cardiorespiratory health with high fidelity. Notably, the generated mechanical movement data may also be used in conjunction with machine-learning algorithms to classify respiratory anomalies, providing an advanced method for early detection of respiratory distress conditions. The technical advantages is accurate and reliable capture of mechanical movement data while minimizing noise.

After the mechanical movement data is generated, the respiratory signal waveforms and cardiac signal waveforms are extracted and segregated. In this context, the term “respiratory signal waveforms” refers to the component of the mechanical movement data associated with breathing movements, which include the expansion and contraction of the thoracic and abdominal cavities during inhalation and exhalation. The respiratory signal waveforms typically exhibit low-frequency oscillations, generally within the range of 0.1 Hz to 0.5 Hz, corresponding to the respiratory rate of the subject. The shape and intensity of respiratory signal waveforms can provide insights into breathing depth, rhythm, and synchrony. The term “heart signal waveforms” refers to another component of the mechanical movement data associated with cardiac activity, including myocardial contractions, valve closures, and blood ejection dynamics. The heart signal waveforms exhibit higher-frequency oscillations, typically ranging between 0.5 Hz and 10 Hz, as they correspond to the rapid mechanical forces generated by each heartbeat. The morphology of heart signal waveforms provides critical insights into heart rate, stroke volume, and cardiac contractility.

Notably, the breathing movements and the cardiac activity differ in frequency, allowing for their separation using appropriate signal processing techniques. For example, respiratory signal waveforms typically have lower frequencies, corresponding to the slow rhythmic expansion and contraction of the thoracic and abdominal cavities during breathing. In contrast, heart signal waveforms have higher frequencies, representing rapid mechanical movements due to cardiac contractions, valve closures, and blood ejection dynamics. As the respiratory signal waveforms are lower-frequency oscillatory waveforms, which can be distinguished from the heart signal waveforms using suitable filtering techniques. It may be appreciated that the suitable filtering techniques comprises at least one of: bandpass filter, notch filter, median filter, least mean squares (LMS) filter, recursive least squares (RLS) filter, empirical mode decomposition (EMD), independent component analysis (ICA), Savitzky-Golay filter and so on. For example, in a subject with obstructive sleep apnoea (OSA), the mechanical movement data (specifically, the respiratory signal waveforms) may indicate periodic cessations of respiration-induced mechanical forces, and such cessation is shown as a flatline morphology in the respiratory signal waveforms. By extracting and analyzing the respiratory signal waveforms, aids in the detection of apnoea episodes and assessment of respiratory health of the subject. It may be appreciated that the suitable filtering techniques can be selected based on the volume of mechanical movement data available. It may be appreciated that in an embodiment, the mechanical movement data is filtered by utilizing a filter configured to operate based on the suitable filtering techniques in order to isolate the respiratory signal waveforms and the heart signal waveforms.

In an embodiment, filtering the mechanical movement data to extract respiratory and heart signal waveforms comprises:

applying a low-pass filter with a cutoff frequency of 1 Hz to isolate the respiratory signal waveforms; and applying wavelet decomposition or empirical mode decomposition (EMD) in the 0.5-1 Hz range to separate overlapping spectral components of breathing and heart signals, thereby isolating the heart signal waveforms.

In this regard, the term "filtering" refers to the process of isolating specific signal components (namely, the heart signal waveforms and the respiratory signal waveforms) based on a parameters (such as frequency, amplitude, wavelength and so on of the heart signal waveforms and the respiratory signal waveforms) from the mechanical movement data to distinguish between respiratory-related and cardiac-related signals. For example, a low-pass filtering is performed utilizing the low-pass filter to extract respiratory signal waveforms by allowing lower frequency components to pass while attenuating higher frequency components. The term "cut-off frequency" refers to the maximum allowable frequency ranges for a signal to pass through the low pass filter without significant attenuation. In other words, the low pass filter allows respiratory signal waveforms of low-frequency components to pass while attenuating higher-frequency components such as the heart signal waveforms. For instance, a Butterworth filter or a finite impulse response (FIR) filter with a cutoff frequency of 1 Hz may be used to isolate breathing-related oscillations or the respiratory signal waveforms. Additionally, to extract heart signal waveforms, wavelet decomposition or empirical mode decomposition (EMD) is applied in the 0.5-1 Hz range to separate overlapping spectral components of breathing and heart signals. The term "wavelet decomposition" refers to a mathematical technique that breaks down a complex signal into multiple frequency sub-bands, allowing the isolation of specific components without losing time-domain resolution. The wavelet decomposition method is particularly useful for analyzing non-stationary signals, such as BCG waveforms, where cardiac and breathing components vary dynamically. Similarly, the EMD is a data-driven technique that decomposes a signal into intrinsic mode functions (IMFs), enabling the separation of the heart signal waveforms and the respiratory signal waveforms. For instance, in a subject with heart failure, EMD can help identify reduced cardiac output by isolating the low-amplitude heart signal waveforms from the high-amplitude respiratory signal waveforms.

In this regard, the term "overlapping spectral components" refers to frequency components within a signal (herein, the mechanical movement data expressed in waveforms) that originate from different physiological sources but share similar frequency ranges, making it difficult to distinguish using basic signal processing techniques. In the context of the mechanical movement data, overlapping spectral components occur when the respiratory signal waveforms and heart signal waveforms exhibit frequency content within a common range, leading to signal interference. For instance, respiratory signals typically fall within the 0.1-0.5 Hz range, while cardiac signals generally exhibit frequencies between 0.5-10 Hz. However, due to natural physiological variations, sensor placement, and motion artifacts, the lower-frequency components of cardiac activity (such as heart rate variability) may overlap with the higher-frequency components of respiratory effort, particularly in the 0.5-1 Hz range. This spectral overlap or overlapping spectral components complicates the separation of these two distinct physiological signals (the respiratory and the heart signal). The technical advantage is accurate separation and extraction of various components (i.e., the heart signal waveforms and respiratory signal waveforms) of the mechanical movement data.

After extraction of the respiratory signal waveforms from the mechanical movement data, the respiratory signal waveforms are decomposed into thoracic, diaphragmatic, and abdominal breathing components based on waveform characteristics and anatomical location of the plurality of BCG sensors. In this regard, the term "thoracic component" refers to a portion of the respiratory signal waveform that originates from rib cage expansion and contraction during breathing of the subject. The thoracic component is primarily detected by the plurality of BCG sensors positioned beneath a scapular region, where movements of the rib cage exert significant mechanical force. In this regard, the term "abdominal component" refers to a portion of the respiratory signal waveform that results from abdominal wall motion due to diaphragmatic contraction. The abdominal component is most prominent in diaphragmatic breathing, where diaphragm associated with the subject moves downward, pushing the abdominal organs outward. Abdominal-dominant breathing is typically observed in restful states, deep breathing exercises, and in individuals with strong diaphragmatic function. The abdominal component is best captured by the plurality of BCG sensors positioned near pelvic or lower lumbar region, where abdominal displacement generates most significant mechanical signal. The term "diaphragmatic component" refers to a portion of the respiratory signal waveform that reflects direct diaphragmatic motion and its influence on both the thoracic and abdominal regions. Unlike the thoracic and abdominal components, which represent surface-level movements, the diaphragmatic component encapsulates the integrated mechanical effect of diaphragmatic contraction on intrathoracic and intra-abdominal pressure dynamics. The diaphragmatic component is critical for detecting diaphragmatic dysfunction, respiratory muscle fatigue, and neuromuscular disorders affecting respiration. The diaphragmatic component is identified through advanced signal processing techniques, such as blind source separation (BSS), which analyze the mixed contributions of different breathing sources across multiple sensor locations.

In this regard, the term "waveform characteristics" refers to unique temporal and morphological attributes of the respiratory signal waveform, which distinguish thoracic, diaphragmatic, and abdominal breathing components. These characteristics include amplitude, frequency, phase relationships, and signal morphology. For example, the amplitude of the respiratory signal waveform indicates breathing effort, with a higher amplitude suggesting deep breathing and a lower amplitude suggesting shallow or restricted breathing.

In this regard, the term "anatomical location" refers to a spatial positioning of the plurality of BCG sensors relative to key respiratory muscle groups, including the thoracic (rib cage), diaphragmatic, and abdominal regions. The placement of the plurality of BCG sensors determines sensitivity and accuracy of detecting each breathing components of the respiratory signal waveforms. For example, thoracic components are most effectively captured by the plurality of BCG sensors positioned near upper back or scapular region, whereas abdominal components are captured by near the lower lumbar or pelvic area. Notably, the diaphragmatic components, which affect both regions, are extracted through multi-sensor signal analysis.

Notably, the mechanical force/movements/vibrations differ in thoracic, diaphragmatic, and abdominal region of the subject's body differ due to their distinct anatomical structures, and physiological functions. For example, the mechanical vibrations in thoracic region are generally higher in frequency but lower in amplitude compared to the mechanical vibrations in diaphragmatic, and abdominal region of the subject's body. Based on the location of the plurality of sensor, morphology and properties of the respiratory signal waveforms, the thoracic, diaphragmatic, and abdominal breathing components are determined and segregated using suitable decomposition techniques, preferably, using blind source separation (BSS) technique.

In an embodiment, decomposing the respiratory signal waveforms comprises applying blind source separation (BSS) techniques, including at least one of: a principal component analysis (PCA), an independent component analysis (ICA), a non-negative matrix factorization (NMF). By applying blind source separation (BSS) techniques (for instance, by applying at least one of PCA, ICA, and NMF), the respiratory signal waveforms are precisely decomposed, thereby allowing for quantitative analysis of respiratory signals. In this regard, the BSS techniques are employed to mathematically separate individual breathing components (i.e., thoracic, diaphragmatic, abdominal breathing components) based on sources (i.e., location of the plurality of BCG sensors) from the respiratory signal waveforms. The technical advantage is that the BSS techniques enable accurate extraction of distinct breathing components, facilitating the identification of breathing abnormalities, thoracoabdominal asynchrony, and respiratory effort distribution.

Notably, the principal component analysis technique refers to a dimensionality reduction technique that transforms the respiratory signal waveforms into orthogonal principal components, ranking them based on variance. Since different breathing components contribute varying amounts of signal energy, PCA identifies dominant modes of respiration by isolating components with the highest variance. For example, in a subject with normal diaphragmatic breathing, PCA may reveal that a first principal component accounts for diaphragmatic expansion, while a second component represents residual thoracic contributions. The independent component analysis technique refers to a statistical technique that assumes that each component of the respiratory signal waveforms is independent and attempts to extract them based on minimizing statistical dependence. Unlike PCA, which finds uncorrelated components, ICA finds truly independent sources, making it highly effective for separating overlapping respiratory signal waveforms. For instance, in cases of asynchronous breathing, where thoracic and abdominal movements occur out of sync, ICA can differentiate these components even if they have similar frequency ranges. The non-negative matrix factorization technique refers to a matrix decomposition technique that assumes that each component of the respiratory signal waveforms contributes non-negative values to the overall breathing signal. NMF is highly effective in estimating relative contributions of thoracic, diaphragmatic, and abdominal breathing by assigning weighting factors to each component. For example, in a healthy subject, NMF may reveal that diaphragmatic breathing contributes 60%, while thoracic breathing contributes 40%. In contrast, in a subject with respiratory muscle fatigue, these percentages may shift, reflecting increased reliance on accessory muscles for breathing.

In an embodiment, decomposing the respiratory signal into thoracic, diaphragmatic and abdominal breathing components comprises:

representing observed signals from the plurality of BCG sensors as a mix of contributions from multiple breathing sources using the equation:

$$X = A \cdot S + N$$

wherein X is a matrix of observed signals from the plurality of BCG sensors, S is underlying source signals corresponding to thoracic, diaphragmatic, and abdominal breathing components, A is a mixing matrix describing the contribution of each source to each sensor and N represents noise and artifacts; and applying the blind source separation techniques to separate the observed signals X into the underlying source signals S, thereby isolating the thoracic, diaphragmatic, and abdominal breathing components.

As a simplified example, consider three ballistocardiography (BCG) sensors placed under a mattress from the shoulder to the pelvis. These sensors capture localized pressure variations caused by respiratory motion. However, each sensor's output is a mixed signal composed of contributions from thoracic, diaphragmatic, and abdominal breathing sources. This relationship can be modelled as:

$$X(t) = X_T(t) + X_D(t) + X_A(t) + \text{Noises } (N)$$

When expressed in matric form:

$$X = \begin{bmatrix} X_T(t) \\ X_D(t) \\ X_A(t) \end{bmatrix} = A \cdot \begin{bmatrix} S_T(t) \\ S_D(t) \\ S_A(t) \end{bmatrix} + N$$

where ST(t): Thoracic breathing waveform, SD(t): Diaphragmatic breathing waveform, SA(t): Abdominal breathing waveform.

An example of a mixing matrix A could be:

$$A = \begin{bmatrix} 0.6 & 0.3 & 0.1 \\ 0.4 & 0.4 & 0.2 \\ 0.2 & 0.5 & 0.3 \end{bmatrix}$$

Each row in A corresponds to a sensor, and each column corresponds to the relative contribution of the thoracic $S_T(t)$, diaphragmatic $S_D(t)$, and abdominal $S_A(t)$ components.

By estimating A and solving for S, BSS methods such as Independent Component Analysis (ICA), Non-negative Matrix Factorization (NMF), or Principal Component Analysis (PCA) can extract the source signals:

$$S(t) = \begin{bmatrix} S_T(t) \\ S_D(t) \\ S_A(t) \end{bmatrix}$$

where: $S_T(t)$: Thoracic breathing waveform, $S_D(t)$: Diaphragmatic breathing waveform, $S_A(t)$: Abdominal breathing waveform.

After the individual breathing components (namely, the thoracic breathing component, the diaphragmatic breathing component and the abdominal breathing component) are extracted, phase differences between the thoracic, diaphragmatic, and abdominal breathing components are analysed. It may be appreciated that the phase differences are estimated over time to quantify a degree of synchrony or asynchrony. In this regard, the term "phase differences" refers to a time delay or shift between oscillatory signals of each component (the thoracic, diaphragmatic, and abdominal breathing components). Each respiratory component of the thoracic, diaphragmatic, and abdominal components exhibits a unique phase relationship during a normal respiratory cycle. For instance, in an ideal synchronized breathing pattern, these components follow a predictable sequence: as the diaphragm contracts and moves downward, the abdominal region expands, followed by thoracic expansion due to rib cage movement. Notably, the ideal synchronized motion suggests efficient lung ventilation and minimal respiratory effort indicating that the subject's cardiorespiratory health is good. However, in cases of possible cardiorespiratory condition or any respiratory impairment, these breathing components may exhibit out-of-phase relationships, leading to asynchrony that can strain respiratory muscles and reduce breathing efficiency.

To quantify a degree of synchrony or asynchrony, the phase differences between the extracted thoracic, diaphragmatic, and abdominal breathing components are analysed over time. In this regard, the term "degree of synchrony and asynchrony" refers to a numerical measure, an index, and so on representing the degree of coordination between different breathing components. Notably, when the phase difference analysis indicates a high phase synchrony between the breathing components, then the degree of synchrony and asynchrony will be of high value indicating normal, well-coordinated breathing, whereas a low value thereof suggests asynchrony and possible cardiorespiratory condition.

For example, in a healthy subject/individual, the thoracic and abdominal breathing components remain in phase, meaning they expand and contract in a coordinated manner. However, in a subject with chronic obstructive pulmonary disease (COPD) or diaphragm dysfunction, phase analysis may reveal that the diaphragmatic component lags behind the thoracic component, indicating delayed diaphragmatic activation. Similarly, in paradoxical breathing, the abdominal and thoracic components move in opposite directions, with abdominal contractions occurring during inhalation instead of expansion, signalling severe respiratory dysfunction.

It may be appreciated that, not only the phase difference between thoracic, abdominal and diaphragmatic breathing components but also analysis of signal waveforms of the thoracic, abdominal and diaphragmatic breathing components, provide valuable insight into the user's cardiorespiratory health. For example, in a clinical situation, just by analysing the signal waveforms of individual components (i.e., thoracic, abdominal and diaphragmatic breathing components) together, valuable insight on user's cardiorespiratory health (for example, paradoxical breathing) can be gained/gathered. In other words, the signal waveforms of the individual components (i.e., thoracic, abdominal and diaphragmatic breathing components) provide valuable insight on user's cardiorespiratory health and aid in making necessary clinical decisions.

In an embodiment, analyzing phase differences between the thoracic, diaphragmatic, and abdominal breathing components over time to quantify synchrony or asynchrony comprises:

- calculating an instantaneous phases of the thoracic, diaphragmatic, and abdominal breathing components using at least one of: Fourier Transform method, Hilbert Transform (HT) method, Hilbert-Huang Transform (HHT) method, Synchro-squeezing Transform method, Short-Time Fourier Transform (STFT) method, Variational Mode Decomposition (VMD) method;
- determining phase differences between the components to detect out-of-phase relationships, wherein out-of-phase relationships indicate variability in phase alignment over time; and
- quantifying the synchrony or asynchrony using a phase synchrony index, wherein the phase synchrony index is a numerical measure of consistency of phase differences, wherein a higher index indicating synchrony and a lower index asynchrony.

In this regard, the instantaneous phases of each component using at least one of signal processing techniques (FT, HT, HHT, Synchro-squeezing Transform, STFT, VMD methods and the likes) is calculated. Since breathing waveforms exhibit cyclic oscillatory behaviour, analysing their instantaneous phase provides insights into how different regions of the body coordinate during respiration. Herein, the term "instantaneous phases" refers to the real-time angular displacement of an oscillatory signal for example, the respiratory signal waveforms. The instantaneous phases are measured in radians or degrees, at any given moment within a cycle. In the context of breathing waveforms, instantaneous phase represents the progression of each breathing component (thoracic, diaphragmatic, and abdominal) through the inhalation and exhalation cycle.

In this regard, the term "Fourier Transform method" refers to a mathematical technique that converts a signal from the time domain to the frequency domain, allowing the identification of dominant frequency components and their phase relationships. In the context of breathing phase analysis, the Fourier Transform helps determine whether the thoracic, diaphragmatic, and abdominal components share a common frequency and phase pattern, or if there is a delay or shift between them. Notably, the term "Hilbert Transform method" is a signal processing technique that extracts the instantaneous amplitude and phase of a signal. It is particularly useful in analyzing non-stationary respiratory signals, where the breathing frequency and phase relationships fluctuate over time. Applying HT method to the thoracic, diaphragmatic, and abdominal signals provides a continuous representation of their phase evolution, enabling precise detection of asynchrony. Further, the term "HHT method" is an advanced time-frequency analysis technique that combines the Hilbert Transform with Empirical Mode Decomposition (EMD) to analyze nonlinear and non-stationary signals. Since breathing waveforms can vary in both frequency and amplitude due to changes in effort, posture, or pathology, the HHT method provides a more adaptive approach to capturing phase relationships compared to traditional Fourier-based methods. The term "Synchro-squeezing Transform method" refers to a refined time-frequency analysis technique that provides higher resolution tracking of phase changes compared to wavelet or Fourier-based approaches. This method is particularly useful in detecting subtle phase variations in breathing patterns, which may indicate early-stage respiratory dysfunction. The term "Short-Time Fourier Transform method" refers to a modification of the Fourier Transform that allows analysis of how phase and frequency components change over a short time windows (ranging between 5 sec to 15 sec). It is beneficial when tracking real-time variations in breathing phase synchrony, particularly in cases where breathing patterns shift due to positional changes, sleep state transitions, or acute respiratory distress. The term "Variational Mode Decomposition method" refers to a signal decomposition technique that extracts intrinsic mode functions (IMFs), allowing for precise separation of thoracic, diaphragmatic, and abdominal components from mixed respiratory waveforms.

Moreover, the instantaneous phases for each breathing components are calculated and then compared with each other, to determine phase differences, which may remain constant in healthy subjects or exhibit out-of-phase relationships in individuals with respiratory impairment. In this regard, the term "out-of-phase relationships" refers to situations where the phase of one breathing component deviates from another, meaning that thoracic, diaphragmatic, and abdominal movements do not follow a synchronized pattern. Normally, during inhalation, the diaphragm contracts, causing both thoracic and abdominal expansion. If these components exhibit phase shifts, such as the abdominal region contracting while the thorax expands, this indicates respiratory asynchrony, which may be associated with neuromuscular disorders, diaphragm fatigue, or obstructive lung diseases.

Further, the phase synchrony index is computed or quantified based on the consistency of phase differences over time, providing a quantitative measure of respiratory coordination. For example, in a patient recovering from lung surgery, phase analysis may show a gradual improvement in synchrony, reflecting improved diaphragmatic engagement. Conversely, in a patient with progressive respiratory muscle fatigue, the phase synchrony index may show a declining trend, indicating worsening asynchrony and a need for intervention.

In this regard, the term "phase synchrony index" refers to a numerical value that quantifies the degree of phase alignment between the thoracic, diaphragmatic, and abdominal breathing components. It may be appreciated that the phase synchrony index defines the degree of synchrony and asynchrony. A higher phase synchrony index indicates that the breathing components remain well-coordinated throughout the respiratory cycle, while a lower phase synchrony index suggests variability, delayed activation, or compensatory breathing patterns. For example, a subject with normal diaphragmatic function would have a high phase synchrony index, whereas a subject with paradoxical breathing due to diaphragm paralysis would show a low phase synchrony index, indicating severe asynchrony.

Upon determining the phase differences between the breathing components (i.e., the thoracic, diaphragmic and abdominal breathing components), relative contributions of thoracic, diaphragmatic, and abdominal breathing components to an overall breathing effort are evaluated, to determine which breathing component is dominating the respiratory signal waveform. The information on dominating breathing component aids in determining underlying a breathing abnormality of the subject. In this regard, the term "overall breathing effort" refers to the combined mechanical effort exerted by different anatomical regions, such as thoracic, diaphragmatic, and abdominal during respiration. Since each breathing component contributes differently based on individual physiology, posture, and respiratory conditions, assessing their relative contributions provides critical insights into respiratory efficiency, effort distribution, and potential dysfunctions. In a healthy individual, breathing effort is well-balanced, with the diaphragm contributing to the majority of respiratory activity, while thoracic and abdominal movements provide supportive expansion and contraction. However, in individuals with respiratory impairment (i.e., breathing abnormality) or cardiorespiratory condition, such as those with chronic obstructive pulmonary disease (COPD), neuromuscular disorders, or post-surgical recovery, the distribution of breathing effort may shift, indicating compensatory breathing patterns, muscle fatigue, or dysfunction in one or more respiratory regions. Thus, breathing abnormalities, such as diaphragmatic weakness, thoracic-dominant breathing, abdominal paradoxical breathing and the likes may be detected by evaluating the relative contributions thoracic, diaphragmatic, and abdominal breathing components.

In an embodiment, evaluating the relative contributions of thoracic, diaphragmatic and abdominal breathing components to an overall breathing effort comprises:

calculating a Breathing Contribution Index (BCI) for each the thoracic, diaphragmatic or abdominal component using the formula:

$$BCI_i = \frac{\sum S_i}{\sum S}$$

wherein $BCI_i$ represents the relative contribution of ith component, $\Sigma S_i$ represents the sum of the extracted signal for the ith component, and $\Sigma S$ represents the overall breathing effort, and wherein the relative contribution of each component is determined as a percentage of the overall breathing effort to evaluate a dominant breathing component.

In this regard, the term "Breathing Contribution Index (BCI)" refers to a quantitative measure that expresses the relative contribution of each breathing component (thoracic, diaphragmatic, or abdominal) to the overall breathing effort. The calculation of the BCI provides a numerical representation of the contribution of each component to the overall breathing effort, enabling identification of dominant breathing patterns, detect abnormalities, and assess respiratory efficiency. Once the BCI values are calculated, the relative percentage contribution of each component is determined to evaluate which region is dominant in respiration. For example, in a healthy individual, the BCI values may show a diaphragmatic contribution of ~60%, thoracic contribution of ~30%, and abdominal contribution of ~10%, reflecting efficient diaphragmatic breathing. However, in the subject with chronic obstructive pulmonary disease (COPD) or asthma, the thoracic component may have an elevated BCI (above 50%), indicating over-reliance on accessory respiratory muscles due to restricted airflow. Additionally, in a patient with diaphragmatic paralysis, the BCI for the diaphragmatic component may drop significantly (~10%), while the thoracic and abdominal components compensate to maintain ventilation.

In this regard, the breathing abnormality is identified based on the analysed phase differences and the evaluated relative contributions. In this regard, the term "breathing abnormality" refers to any deviation from normal respiratory mechanics, including asynchrony, inefficiency, or irregular effort distribution among the thoracic, diaphragmatic, and abdominal components. Notably, the breathing abnormality may manifest as a phase desynchronization, where the thoracic, diaphragmatic, and abdominal components move out of sync, indicating thoracoabdominal asynchrony, an imbalanced effort distribution, where one component contributes disproportionately compared to the others, suggesting respiratory muscle weakness, airway obstruction, or compensatory breathing mechanisms, and an erratic phase shifts, where the respiratory cycle exhibits sudden or irregular phase changes, which may be a sign of neurological dysfunction, fatigue, or respiratory distress and the likes. By identifying the breathing abnormality, early detection of cardiorespiratory conditions, continuous monitoring of disease progression, and timely therapeutic interventions may be facilitated. The technical advantage is quantification of obtained information (i.e., the relative contributions of thoracic, diaphragmatic and abdominal breathing components) from the mechanical movement data, for ease of further analysis.

In an embodiment, identifying the breathing abnormality comprises:

- detecting asynchrony between thoracic, diaphragmatic and abdominal breathing components based on the analysed phase differences;
- identifying imbalance in the relative contributions of thoracic, diaphragmatic and abdominal components to the overall breathing effort; and
- classifying the detected asynchrony and the identified imbalance as the breathing abnormality.

In this regard, detection of asynchrony between the thoracic, diaphragmatic, and abdominal breathing components is based on the analysed phase differences that depict whether the components exhibit delayed activation, out-of-phase relationships, or irregular phase shifts during respiration. In normal breathing, these components maintain a consistent phase relationship, whereas in conditions such as diaphragmatic dysfunction or paradoxical breathing, the phase alignment is disrupted, leading to inefficient respiration. Moreover, based on the detection of asynchrony an identification of imbalance in the relative contributions of the thoracic, diaphragmatic, and abdominal components to the overall breathing effort is performed. Herein, the identification involves evaluation of how much each component contributes to overall breathing efforts. Further, the detected asynchrony and the identified imbalance is classified as a breathing abnormality based on the correlating the findings with predefined respiratory conditions, wherein the system determines whether the detected phase shifts and effort imbalances meet the criteria for thoracoabdominal asynchrony, paradoxical breathing, or restrictive breathing patterns. The technical advantage is accurate identification of the breathing abnormality.

In an embodiment, the method further comprises:

- employing a machine learning model trained on labelled datasets of breathing patterns to classify normal and abnormal breathing patterns; and
- detecting the breathing abnormality, using the analysed phase differences and the evaluated relative contributions as input features, to identify the potential cardiorespiratory condition.

In this regard, employing the machine learning model trained on labelled datasets of breathing patterns to classify normal and abnormal breathing patterns comprises utilizing a supervised learning approach. The machine learning model is trained on a dataset containing pre-annotated respiratory signal waveforms that may correspond to normal and abnormal breathing patterns. The dataset includes labelled instances of synchronized and asynchronized breathing, as well as variations in thoracic, diaphragmatic, and abdominal contributions, enabling the machine learning model to learn characteristic features of healthy and dysfunctional respiration. The machine learning model extracts key signal attributes such as instantaneous phase shifts, breathing effort distribution, waveform morphology, and spectral features, and applies classification algorithms such as neural networks, support vector machines (SVMs), or decision trees to distinguish between normal and pathological breathing behaviours. Through iterative training and validation, the machine learning model enhances its accuracy in recognizing early-stage respiratory dysfunctions, improving ability to provide real-time assessment of cardiorespiratory health.

Notably, detecting the breathing abnormality, using the analysed phase differences and the evaluated relative contributions as input features, to identify the potential cardiorespiratory condition involves integrating multiple physiological markers derived from phase synchrony analysis and Breathing Contribution Index (BCI) evaluation. These extracted features serve as inputs to the trained machine learning model, which classifies the breathing pattern and maps it to specific cardiorespiratory conditions, such as obstructive sleep apnoea (OSA), chronic obstructive pulmonary disease (COPD), respiratory muscle fatigue, or paradoxical breathing due to neuromuscular disorders. By leveraging machine learning-driven classification, the system ensures high-precision detection of respiratory abnormalities, supporting early intervention, personalized treatment recommendations, and long-term monitoring and assessment of cardiorespiratory health.

It may be appreciated that based on the identified breathing abnormality, a potential cardiorespiratory condition can be detected. In this regard, the term "potential cardiorespiratory condition" refers to any physiological impairment or pathological state affecting the integrated function of the respiratory and cardiovascular systems, characterized by abnormal breathing mechanics, altered phase relationships, and disproportionate breathing effort distribution. The potential cardiorespiratory condition may be identified based on the identified breathing abnormality. For example, a subject with an intermittent phase disruptions and sudden reductions in diaphragmatic effort during sleep, the potential cardiorespiratory condition may be detected as with obstructive sleep apnoea (OSA).

In an embodiment, the potential cardiorespiratory condition comprises: chronic obstructive pulmonary disease (COPD), sleep apnoea, diaphragmatic dysfunction, respiratory muscle fatigue, asthma, hyperventilation and cardiovascular conditions. In this regard, throughout the present disclosure the term "chronic obstructive pulmonary disease" refers to a progressive lung disease characterized by persistent airflow obstruction, reduced lung elasticity, and increased respiratory effort. COPD alters normal breathing mechanics, often leading to thoracic-dominant breathing, where the BCI for thoracic effort is disproportionately high, and the diaphragmatic contribution is significantly reduced. Patients with COPD often exhibit shortness of breath, increased respiratory rate, and inefficient ventilation, which can be identified through phase misalignment and effort imbalances in the recorded BCG waveforms. Notably, the term "sleep apnoea" refers to a sleep-related breathing disorder where repeated episodes of apnoea (cessation of breathing) or hypopnea (shallow breathing) occur due to upper airway obstruction or neurological dysfunction. In obstructive sleep apnoea (OSA), breathing patterns become irregular, with intermittent loss of diaphragmatic effort followed by exaggerated recovery breaths. Notably, the term "diaphragmatic dysfunction" refers to a condition where the diaphragm fails to contract effectively, leading to insufficient lung expansion and impaired ventilation. This dysfunction may be partial (diaphragmatic weakness) or complete (diaphragmatic paralysis). The term "respiratory muscle fatigue" refers to a state where the respiratory muscles, including the diaphragm and intercostal muscles, become exhausted due to sustained high effort or inadequate oxygen supply. Respiratory muscle fatigue is commonly seen in prolonged respiratory distress, severe lung infections, or neuromuscular disorders, where the breathing pattern becomes unstable and inefficient over time. The term "asthma" refers to a chronic inflammatory disorder of the airways, characterized by episodic bronchoconstriction, airflow limitation, and increased respiratory effort.

The term "hyperventilation" refers to a breathing abnormality where the subject breathes excessively fast or deep, leading to decreased carbon dioxide ($CO_2$) levels in the blood. Hyperventilation is often associated with anxiety, panic disorders, metabolic imbalances, or neurological conditions, and can lead to dizziness, shortness of breath, and muscle spasms due to $CO_2$ depletion. To that end, the term "cardiovascular conditions" refers to a broad category of heart and circulatory disorders that affect respiratory function due to compromised blood flow, oxygen delivery, or autonomic regulation. Using breathing abnormality to identify the potential cardiorespiratory condition, provides accurate and reliable assessment of subject's cardiorespiratory health. The technical advantage is accurate and reliable assessment of subject's cardiorespiratory health.

In an embodiment, detecting the potential cardiorespiratory condition comprises:

correlating the identified breathing abnormality with a predefined cardiorespiratory condition; and detecting the potential cardiorespiratory condition based on the correlated abnormality.

In this regard, correlating the identified breathing abnormality with a predefined cardiorespiratory condition involves analyzing the phase differences, effort imbalances, and waveform irregularities in identified breathing abnormality associated with the subject and matching them with the predefined cardiorespiratory condition associated with specific cardiorespiratory disorders. The term "predefined cardiorespiratory condition" refers to a specific respiratory or cardiovascular disorder that has been previously categorized based on established clinical guidelines, medical diagnostic criteria, and known pathophysiological patterns. These conditions serve as reference disorders against which detected breathing abnormalities are correlated to determine a potential diagnosis. Each of the predefined cardiorespiratory condition can be associated with distinct breathing abnormality and a breathing pattern thereof, such as phase desynchronization, irregular breathing effort distribution, and waveform abnormalities, which can be identified through phase difference analysis. Notably, based on the phase difference and the evaluated Breathing Contribution Index (BCI), the identified breathing abnormality with the predefined cardiorespiratory condition. It may be appreciated that machine learning-models can also be employed to corelate identified breathing abnormality with the predefined cardiorespiratory condition. For example, COPD is characterized by thoracic-dominant breathing with reduced diaphragmatic contribution, while sleep apnoea is identified by episodic suppression of diaphragmatic movement followed by compensatory hyperventilation. Corelating breathing abnormality with the predefined cardiorespiratory condition aids in determining cardiorespiratory health of the subject, with accuracy and reliability.

Notably, the correlation may be performed based on the machine learning models, predefined clinical thresholds, and statistical pattern recognition algorithms to compare the subject's breathing characteristics against a database of known respiratory and cardiovascular conditions. For example, if the detected abnormality includes reduced diaphragmatic contribution (low BCI), increased thoracic effort, and paradoxical abdominal motion, it may be correlated with diaphragmatic dysfunction or neuromuscular respiratory failure. Notably, detecting the potential cardiorespiratory condition based on the correlated abnormality comprises classifying the subject's respiratory dysfunction into a specific disease category, such as chronic obstructive pulmonary disease (COPD), sleep apnoea, respiratory muscle fatigue, or cardiovascular-induced breathing irregularities. For instance, if the system detects irregular breathing effort with episodic phase misalignment, it may classify the condition as obstructive sleep apnoea (OSA), prompting further sleep study recommendations. The technical advantage is accurate assessment of any underlying cardiorespiratory condition of the subject.

In an embodiment, the method further comprises removing noise data segments, from the mechanical movement data, caused by large-scale non-beathing movements using at least one of: applying a spectral approach, employing an unsupervised learning model or employing a supervised learning model. In this regard, the term "noise data segments" refers to portions of the mechanical movement data that contain signal artifacts unrelated to physiological activities such as respiration and cardiac function. The signal artifacts are primarily caused by large-scale non-breathing movements, including shifting positions during sleep, limb movements, bed exits, or external vibrations affecting the plurality of BCG sensors. For instance, if the subject momentarily shifts their body position or adjusts their posture, the mechanical movement data may exhibit a sudden increase in signal amplitude across a broad frequency range. Since large scale movements introduce abrupt, high-amplitude variations in the recorded signal, they can obscure finer/minute oscillations associated with breathing and cardiac activity, leading to inaccurate assessments of respiratory activity, heart rate variability.

Further, the noise data segments are removed using the spectral approach. In this regard, the term "spectral approach" refers to a frequency-domain analysis technique used to differentiate between desired respiratory signals and the noise data segments within the mechanical movement data. The spectral approach involves analyzing power distribution of the generated mechanical movement data across different frequency bands to identify and remove the noise data segments dominated by large-scale non-beathing body movements. For example, the large-scale non-beathing body movements often generate high-energy components at irregular frequencies, whereas respiratory and cardiac signals exhibit well-defined frequency characteristics within predictable ranges. Furthermore, unsupervised learning model, such as clustering algorithms (e.g., K-means or DBSCAN) or principal component analysis (PCA), analyzing patterns within the mechanical movement data and removing the noise data segments that deviate from expected physiological signals. The unsupervised learning models are particularly useful when no labelled training data is available, as they can automatically group similar data points and classify abnormal motion artifacts as noise.

Alternatively, the method can employ the supervised learning model, such as a neural network or a binary classifier (e.g., support vector machines (SVM) or decision trees) trained on labelled datasets of clean and noisy mechanical movement data. The supervised models use pre-existing data annotations to differentiate between valid respiratory and cardiac signals and noise data, ensuring that only meaningful physiological signals are retained for analysis by removing the noise data segments from the mechanical movement data. For example, in a sleep monitoring application, an unsupervised learning model can identify patterns of bed exits or abrupt posture shifts by detecting high-amplitude transient signals and classifying them as the noise data segments. Similarly, in a hospital-based cardiorespiratory monitoring system, a supervised learning model trained on patient movement data can automatically exclude the noise data segments associated with sensor disturbances caused by medical staff interactions or equipment adjustments. The technical advantage is noise removal for ease of further analysis.

In an embodiment, the method further comprises:

generating an alert for a user and a medical professional upon identifying the potential cardiorespiratory condition;

providing detailed reports to the medical professional to assist in diagnosis and treatment planning for the potential cardiorespiratory condition.

In this regard, the term "alert" refers to an automated notification generated detecting the potential cardiorespiratory condition or abnormal breathing pattern, which is communicated to the user and/or medical professional via a secure platform. The alert may indicate real-time respiratory irregularities, worsening phase desynchronization, or significant changes in breathing effort distribution, prompting timely medical intervention or further assessment. The alert may be generated for notifying the user in real-time. The identification and notification is performed to inform the user and the medical professional when a breathing abnormality is correlated with a predefined cardiorespiratory condition. Herein the term "user" refers to an individual whose respiratory and cardiac functions are being monitored using the system. The user may be a patient diagnosed with or at risk of developing a cardiorespiratory condition, an individual undergoing respiratory therapy or rehabilitation, or a healthy individual utilizing the system for proactive health monitoring. The user interacts with the system through alerts, reports, and real-time respiratory insights, enabling self-monitoring and early awareness of potential breathing abnormalities. Notably, the term "medical professional" refers to a licensed healthcare provider responsible for diagnosing, managing, and treating respiratory and cardiovascular conditions based on the data collected by the system. This includes, but is not limited to, pulmonologists, cardiologists, sleep specialists, respiratory therapists, general physicians, and critical care doctors.

Upon identifying the potential cardiorespiratory condition, the alert (such as a text message, a visual alert, a haptic alert, an audio alert) may be automatically triggered, which may be sent via mobile application, email, SMS, or integrated hospital monitoring systems. It may be appreciated that the alert may be a blink of light, flashing in a monitor, a vibration on a device such as a pager, mobile phone, smart phone, smart wristwatch, a ringing or siren, a text on the monitor, the mobile phone, smart phone, or smart wristwatch or and so on. It may be appreciated that the alert can indicate the severity, frequency, and progression of the detected abnormality, allowing for timely intervention and medical assessment. For example, in a subject exhibiting severe sleep apnoea episodes, an urgent alert may be generated recommending immediate clinical evaluation or adjustments in treatment, such as continuous positive airway pressure (CPAP) therapy modifications.

Further, providing detailed reports to the medical professional to assist in diagnosis and treatment planning for the potential cardiorespiratory condition comprises compiling and structuring comprehensive respiratory data for clinical review. The detailed reports may be visual or auditory containing breathing waveform analysis, phase difference trends, Breathing Contribution Index (BCI) values, and historical progression of the detected abnormality. The detailed reports provide healthcare professionals with quantitative and graphical insights into the subject's respiratory mechanics, enabling data-driven clinical decision-making. For example, in a patient with progressive respiratory muscle fatigue, the report may illustrate a declining diaphragmatic contribution over time, allowing the physician to adjust treatment strategies, such as recommending pulmonary rehabilitation or ventilatory support. The technical advantage is monitoring subject's condition with required vigilance thereby minimizing possible risks.

In an embodiment, the method further comprises:

storing historical data, including the analysed phase differences, the evaluated relative contributions and the identified breathing abnormality, in a secure database for long-term monitoring and progression of the detected potential cardiorespiratory condition; and providing access to the stored data to the user and the medical professional through a secure platform to assess the progression of the detected potential cardiorespiratory condition.

In this regard, the term "historical data" refers to previously recorded and time-stamped mechanical movement data, including analysed phase differences, evaluated relative contributions, and identified breathing abnormalities, that are securely stored for long-term monitoring, trend analysis, and disease progression tracking. The historical data further comprises continuously recording breathing metrics, phase synchrony trends, and waveform characteristics to maintain data integrity, accessibility in future. The historical data enables identifying patterns of deterioration, improvement, or stability in the subject's cardiorespiratory health over extended periods, supporting early intervention and personalized treatment adjustments. For example, in a subject with diaphragmatic dysfunction, historical data may reveal a progressive decline in diaphragmatic contribution (BCI) over several months, prompting a physician to recommend respiratory therapy before severe impairment occurs. For another example, a subject diagnosed with obstructive sleep apnoea (OSA) may have their breathing patterns stored over time, which allows the medical professional to track a severity the sleep apnoea, to monitor and effectiveness of CPAP therapy, and to detect any worsening of breathing effort imbalances.

Figure 2:
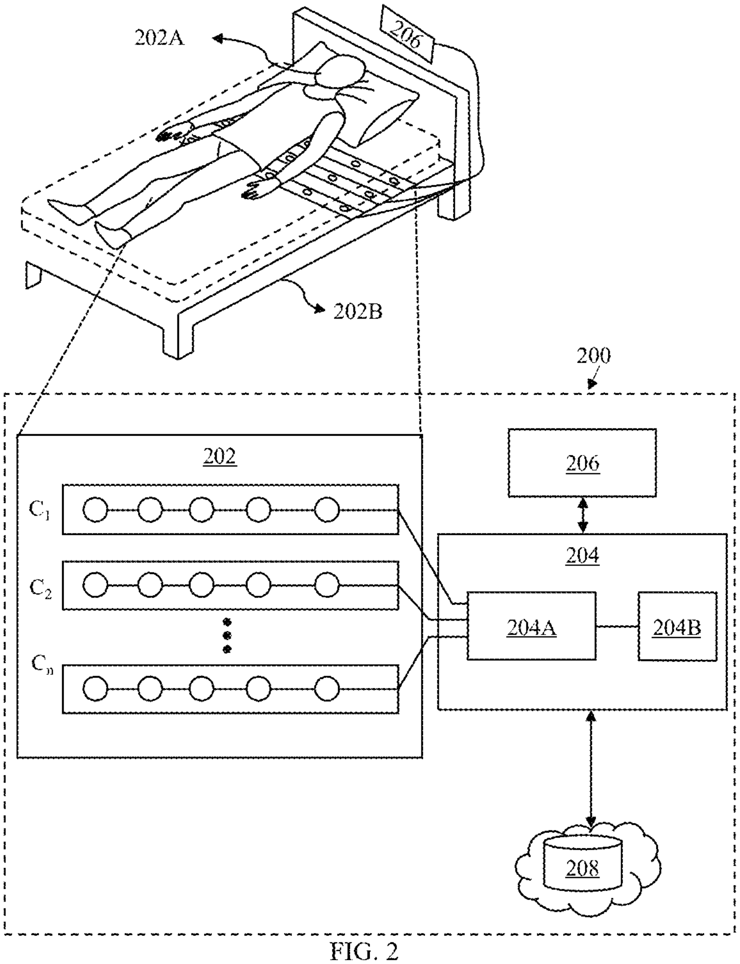
FIG. 2 illustrates schematic illustration of an implementation of a system for assessing cardiorespiratory health, in accordance with an embodiment of the present disclosure.

It may be appreciated that the historical data is stored in the secure database for long-term monitoring and progression of the detected potential cardiorespiratory condition. Notably, the historical data stored in the secured database can be accessed by authenticated user thereby providing data security and privacy protection to the subject. In this regard, the medical professional can be provided with authentication to access to the stored historical data through a secure platform to assess the progression of the detected potential cardiorespiratory condition. In this regard, the term "secure database" refers to a data storage and retrieval system designed and implemented with security measures to protect data from unauthorized access, tampering, theft, or corruption. The term secured platform refers to protected digital interface that can be used to access the secured database. Notably, the secured platform is configured to provide authorized access to store retrieve various cardiorespiratory health data (i.e., mechanical movement data, analysed phase differences, the evaluated relative contributions and the identified breathing abnormality) while ensuring data privacy, integrity, and compliance with security regulations. The secure platform may be a cloud-based portal, encrypted local server, or mobile application that provides real-time and historical respiratory insights to both the user and medical professional. The secure platform incorporates access controls, encryption protocols, authentication mechanisms, and compliance with medical data protection standards (e.g., HIPAA, GDPR) to prevent unauthorized access or data breaches. For example, a pulmonologist reviewing a patient's sleep apnoea history can securely access the stored phase synchrony trends and Breathing Contribution Index (BCI) data via the secure platform, ensuring confidentiality and reliability in clinical decision-making. The technical advantage of storing historical data in the secure database is that this ensures that mechanical movement data can be retrieved and analysed to assess progressive changes in cardiorespiratory health when required even remotely via a suitable network connection With reference to FIG. 2, illustrated is a schematic illustration of an implementation of a system 200 for assessing cardiorespiratory health, in accordance with an embodiment of the present disclosure. As shown, the system 200 comprises a plurality of BCG sensors 202, a processor 204, a user interface 206 and a storage 208. It may be appreciated that the system 200 is configured to use the aforementioned method for assessing cardiorespiratory health.

In this context, the processor 204 refers to an electronic component in of the system 200 that is configured to executes specific functions necessary for operation of the system 200. Notably, the processor 204 may be a microcontroller, microprocessor, an on-chip control unit, a central processing unit, or any such suitable arrangement capable of receiving input, analyze the input received, and perform required operation thereafter. In an embodiment, the processor 204 maybe onboard the user interface 206. In other words, the processor 204 may be s integrated directly into the user interface 206 rather than being a separate component.

In an embodiment, the system 200 is implemented in an environment designed for continuous, non-contact cardiorespiratory monitoring, comprising, a support surface 202B wherein the plurality of BCG sensors 202 may be embedded. Notably, the support surface 202B serves as a physical structure on which the subject 202A rests, facilitating the detection of mechanical forces generated by breathing movements. While the support surface 202B is typically a bed, it may also be a sofa, orthopaedic mattress, chair, or any surface where the torso of the subject's 202A body can be rested, enabling flexible deployment across various settings such as home environments, hospitals, sleep clinics, and assisted living facilities.

It may be appreciated that the plurality of BCG sensors 202 embedded in the support surface 202A (for example, the plurality of BCG sensors are arranged beneath a mattress or bedding), detects subtle vibrations induced by thoracic, diaphragmatic and abdominal movements during various respiratory and cardiac activities.

In an embodiment the plurality of BCG sensors 202 is arranged in a grid pattern on a support surface 202B with a spacing of 10-15 cm to cover a thoracic, a diaphragmatic and an abdominal region for detection of the mechanical forces caused by the breathing movements. In this regard, the grid pattern arrangement of the plurality of BCG sensors 202 is designed to ensure optimal coverage of the torso of the subject 202A, specifically targeting three key anatomical regions including the thoracic region (upper chest), the diaphragmatic region (midsection), and the abdominal region (lower torso). Moreover, the plurality of BCG sensors 202 are arranged in a manner where each BCG sensor is spaced apart from the other by the spacing of range from 10 to 15 cm, for efficient capture of mechanical movement data. In this regard, the term "spacing" refers to space between the plurality of BCG sensor 202. For example, as shown in the FIG. 2, the space between C1 sensors and C2 sensors of the plurality of BCG sensors 202 may be 10-15 cm. The precise placement of plurality of BCG sensors 202 ensures that each respiratory source contributes to the detected signal. The technical advantage of such grid pattern arrangement is that high-quality detection of mechanical forces can be performed, allowing for an accurate differentiation of thoracic, diaphragmatic, and abdominal breathing components.

Since the plurality of BCG sensors 202 is positioned beneath the mattress or bedding, the system 200 remains entirely non-contact, making it comfortable for continuous monitoring in both clinical and home settings. The support surface 202B (bed) serves as a stable medium for transmitting mechanical forces, allowing the BCG sensors to detect subtle body vibrations caused by inhalation and exhalation without requiring direct attachment to the subject 202A. The non-invasive nature of the sensor placement eliminates the need for wearable belts or intrusive monitoring equipment, reducing user discomfort and improving compliance for long-term respiratory health tracking. Notably, the subject 202A lies on the support surface 202B, with their torso positioned above the plurality of BCG sensors 202, which are placed beneath the mattress or bedding or cushioning placed on the support surface. This arrangement enables the system 200 to capture mechanical forces generated by the subject's respiratory activity in a non-contact manner.

Furthermore, the grid configuration enhances signal accuracy and spatial resolution, enabling the system 200 to distinguish between synchronized and asynchronous breathing patterns across different regions of the torso. Notably, by implementing the sensor spacing grid pattern beneath the mattress, the system 200 enables precise respiratory monitoring without disrupting the subject's natural sleeping posture or daily routine. This configuration supports real-time analysis of breathing phase relationships, breathing effort distribution, and the detection of potential cardiorespiratory abnormalities, thereby facilitating early diagnosis, personalized respiratory therapy, and continuous health monitoring.

The plurality of BCG sensors 202 generate analog mechanical movement data, which is then amplified by an amplifier 204A (such as an LNA) to enhance quality thereof and reduce noise. The amplified signals are converted into digital form by an analog-to-digital converter (ADC) 204B, for ease of analysis thereby enabling advanced signal processing, phase analysis, and breathing effort evaluation. Notably, the processor 204 is configured to executed steps of the aforementioned method to predict the potential cardiorespiratory conditions that the subject 202A may have. In this regard, the processor 204 is operatively connected to the plurality of BCG sensors 202, the amplifier 204A and the ADC 204B and is configured to receive the mechanical movement data generated. Moreover, the processor 204 is also configured to filter the mechanical movement data to extract respiratory signal waveforms and heart signal waveforms. The processor 204 is also configured to decompose the respiratory signal waveforms into thoracic, diaphragmatic, and abdominal breathing components based on waveform characteristics and anatomical location of the plurality of BCG sensors 202. Further, the processor 204 is configured to analyse phase differences between the thoracic, diaphragmatic, and abdominal breathing components over time to quantify a degree of synchrony or asynchrony. Furthermore, the processor 204 is configured to evaluate relative contributions of thoracic, diaphragmatic, and abdominal breathing components to an overall breathing effort. Furthermore, the processor 204 is configured to identify breathing abnormality based on the analysed phase differences and the evaluating relative contributions and detect a potential cardiorespiratory condition based on the identified breathing abnormality.

It may be appreciated that the processor 204 is also communicably coupled to the storage 208 for receiving additional input, for example, the processor 204 is configured to receive processed data (i.e., historical data, corresponding cardiorespiratory health data, and historical mechanical movement data from the storage 208) for more accurate analysis when required. The processed data can be transmitted to a user interface 206 for the medical professional to review. The user interface 206 is at least one of: a smartphone application, a tablet, a desktop dashboard, or an integrated hospital monitoring system, allowing both the subject 202A and the medical professionals to access real-time respiratory insights.

The system 200 further includes the storage 208, which may be a cloud-based database, local encrypted storage, or hospital server, ensuring secure, long-term data retention. This enables the system 200 to track historical breathing patterns, monitor disease progression, and support AI-driven predictive analysis for early intervention in cardiorespiratory disorders. For example, a sleep specialist monitoring a patient with obstructive sleep apnoea (OSA) can retrieve historical data from storage 208, analyze phase synchrony trends, and adjust CPAP therapy accordingly.

In an embodiment, the processing unit processor is configured to employ a machine learning model trained on labelled datasets of breathing patterns to classify normal and abnormal breathing patterns, and wherein the processor is configured to detect breathing abnormality using the analysed phase differences and the evaluated relative contributions as input features to identify the potential cardiorespiratory condition. In this regard, it may be appreciated that the processor 204 is configured to employ a machine learning model to perform steps of the aforementioned method for assessing cardiorespiratory health and determine a potential cardiorespiratory condition of the subject 202A. The technical advantage is minimization of human effort associated for accurate assessment of cardiorespiratory health.

In an embodiment, the plurality of BCG sensors is configured to capture observed signals as a mix of contributions from multiple breathing sources, and the processor is configured to apply blind source separation techniques to separate the observed signals into underlying source signals, thereby isolating thoracic, diaphragmatic, and abdominal breathing components.

In an embodiment, the processor is configured to calculate a Breathing Contribution Index (BCI) for each of thoracic, diaphragmatic, or abdominal breathing component, and determine the relative contribution of each component as a percentage of the overall breathing effort to identify a dominant breathing component.

In an embodiment, the processor is configured to:

calculate instantaneous phases of the thoracic, diaphragmatic and abdominal breathing components using at least one of: Fourier Transform method, Hilbert Transform (HT) method, Hilbert-Huang Transform (HHT) method, Synchro-squeezing Transform method, Short-Time Fourier Transform (STFT) method, Variational Mode Decomposition (VMD) method;

determine phase differences to detect out-of-phase relationships; and quantify synchrony or asynchrony using a phase synchrony index, wherein the phase synchrony index is a numerical measure of consistency of phase differences.

It may be appreciated that various embodiments and variants disclosed above, with respect to the aforementioned method, apply mutatis mutandis to the system 200 as well.

Figure 3:
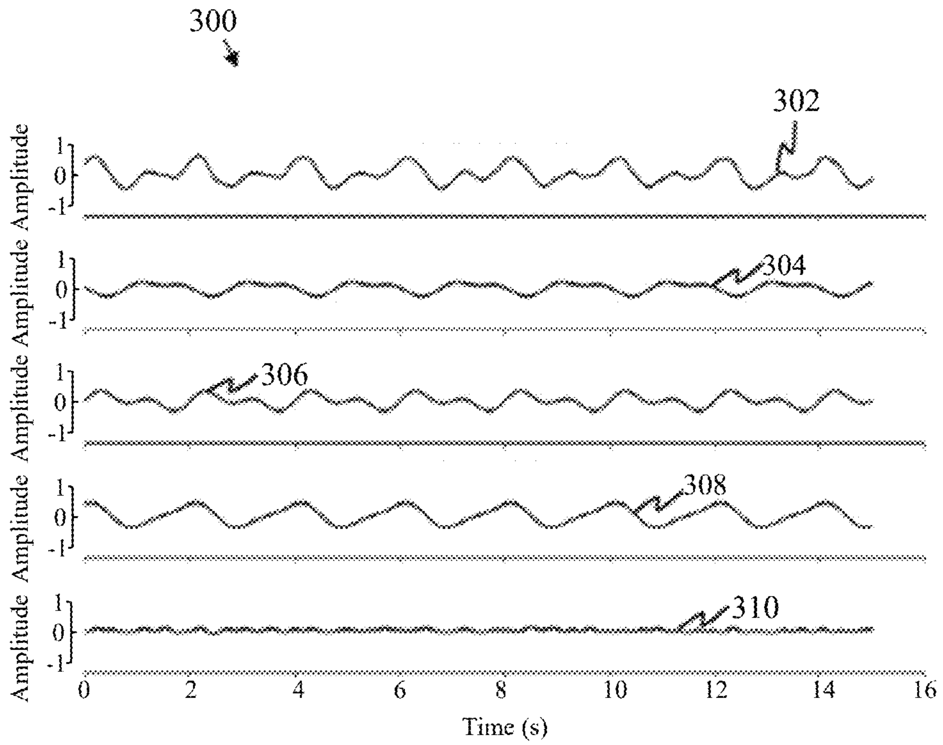
FIG. 3 illustrates a schematic illustration depicting the morphology of a respiratory signal waveform and various signal components obtained through decomposition of the respiratory signal waveform, in accordance with an embodiment of the present disclosure.

Referring to FIG. 3, illustrated is a schematic illustration 300 depicting the morphology of a respiratory signal waveform and various signal components obtained through decomposition of the respiratory signal waveform, in accordance with an embodiment of the present disclosure. In this regard, the respiratory signal waveform is decomposed into a thoracic breathing component, a diaphragmatic breathing component, an abdominal breathing component and noise. As shown, the X-axis represent time, and the Y-axis represents amplitude of the signal waveforms (namely, the respiratory signal waveform, the thoracic breathing component, the diaphragmatic breathing component, the abdominal breathing component and the noise). As shown, a curve 302 shows the morphology of the respiratory signal waveforms obtained by filtering the mechanical movement data. Similarly, curve 304, curve 306 and curve 308 show the morphology of the thoracic, diaphragmatic, and abdominal breathing components respectively. As shown, curve 310 represents noise that may be present in the respiratory signal waveform. In this regard, when a user experience breathing difficulties due to sleep apnoea, the morphologies of the curves 302, 304, 306 and 308 also change correspondingly, i.e., the morphologies (shape of the signals) of the curves 302, 304, 306 and 308 show deviation from normal shape. Therefore, based on the time (when breathing disturbance has happened), how much deviation is observed, and how frequent such deviations are there, cardiorespiratory health can be accurately assessed.

Modifications to embodiments of the invention described in the foregoing are possible without departing from the scope of the invention as defined by the accompanying claims. Expressions such as “including”, “comprising”, “incorporating”, “consisting of”, “have”, “is” used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The invention claimed is:

1. A method for assessing cardiorespiratory health, the method comprising:

acquiring, via a plurality of ballistocardiography (BCG) sensors embedded in a support surface and positioned to correspond to thoracic, diaphragmatic, and abdominal regions of a torso of the subject, analog signals representing mechanical forces generated by respiratory and cardiac activity of the subject;

amplifying the analog signals using at least one low-noise amplifier and digitizing the amplified signals using at least one analog-to-digital converter (ADC) to generate mechanical movement data;

filtering, by a processor, the mechanical movement data to extract respiratory signal waveforms and heart signal waveforms;

decomposing, by the processor, the respiratory signal waveforms into thoracic, diaphragmatic, and abdominal breathing components based on waveform characteristics and anatomical location corresponding to the plurality of BCG sensors;

analyzing, by the processor, phase differences between the thoracic, diaphragmatic, and abdominal breathing components over time to quantify a degree of synchrony or asynchrony;

evaluating, by the processor, relative contributions of thoracic, diaphragmatic, and abdominal breathing components to an overall breathing effort;

identifying, by the processor, a breathing abnormality based on the analysed phase differences and the evaluated relative contributions;

detecting, by the processor, a potential cardiorespiratory condition based on the identified breathing abnormality; and generating, by the processor, an alert based on the detected potential cardiorespiratory condition.

2. The method of claim 1, wherein the plurality of BCG sensors is arranged in a grid pattern on the support surface with a spacing of 10 to 15 cm to cover the thoracic, diaphragmatic, and abdominal regions of the torso.

3. The method of claim 1, further comprising removing noise data segments, from the mechanical movement data, caused by large-scale non-breathing movements using at least one of: applying a spectral approach, employing an unsupervised learning model or employing a supervised learning model.

4. The method of claim 1, wherein identifying the breathing abnormality comprises:

employing a machine learning model trained on labelled datasets of breathing patterns to classify normal and abnormal breathing patterns, wherein the machine learning model uses the analysed phase differences and the evaluated relative contributions as input features to identify the breathing abnormality.

5. The method of claim 1, further comprising:

sending the alert to a user and a medical professional upon detecting the potential cardiorespiratory condition; and providing detailed reports to the medical professional to assist in diagnosis and treatment planning for the potential cardiorespiratory condition.

6. The method of claim 5, further comprising:

storing historical data, including the analysed phase differences, the evaluated relative contributions and the identified breathing abnormality, in a secure database for long-term monitoring and progression of the detected potential cardiorespiratory condition; and providing access to the stored data to the user and the medical professional through a secure platform to assess the progression of the detected potential cardiorespiratory condition.

7. The method of claim 1, wherein decomposing the respiratory signal waveforms comprises applying blind source separation techniques, including at least one of: a principal component analysis (PCA), an independent component analysis (ICA), a non-negative matrix factorization (NMF).

8. The method according to claim 7, wherein decomposing the respiratory signal waveforms into thoracic, diaphragmatic and abdominal breathing components comprises:

representing observed signals from the plurality of BCG sensors as a mix of contributions from multiple breathing sources using the equation:

$$X = A \cdot S + N,$$

wherein X is a matrix of observed signals from the plurality of BCG sensors, S is a matrix of underlying source signals corresponding to thoracic, diaphragmatic, and abdominal breathing components, A is a mixing matrix describing the contribution of each source to each sensor and N represents noise and artifacts; and applying the blind source separation techniques to separate the observed signals X into the underlying source signals S, thereby isolating the thoracic, diaphragmatic, and abdominal breathing components.

9. The method of claim 1, wherein evaluating the relative contributions of thoracic, diaphragmatic and abdominal breathing components to an overall breathing effort comprises:

calculating a Breathing Contribution Index (BCI) for each of the thoracic, diaphragmatic or abdominal breathing component using the formula:

$$BCI_i = \sum S_i / \sum S,$$

wherein $BCI_i$ represents the relative contribution of $i^{th}$ component, $\Sigma S_i$ represents the sum of the extracted signal for the $i^{th}$ component, and $\Sigma S$ represents the overall breathing effort, and wherein the relative contribution of each component is determined as a percentage of the overall breathing effort to evaluate a dominant breathing component.

10. The method of claim 1, wherein the potential cardiorespiratory condition comprises: chronic obstructive pulmonary disease (COPD), sleep apnoea, diaphragmatic dysfunction, respiratory muscle fatigue, asthma, hyperventilation and cardiovascular conditions.

11. The method of claim 1, wherein filtering the mechanical movement data to extract the respiratory signal waveforms and heart signal waveforms comprises:

applying a low-pass filter with a cutoff frequency of 1 Hz to isolate the respiratory signal waveforms; and applying wavelet decomposition or empirical mode decomposition (EMD) in the 0.5-1 Hz range to separate overlapping spectral components of breathing and heart signals, thereby isolating the heart signal waveforms.

12. The method of claim 1, wherein analyzing phase differences between the thoracic, diaphragmatic, and abdominal breathing components over time to quantify a degree of synchrony or asynchrony comprises:

calculating instantaneous phases of the thoracic, diaphragmatic, and abdominal breathing components using at least one of: Fourier Transform method, Hilbert Transform (HT) method, Hilbert-Huang Transform (HHT) method, Synchro-squeezing Transform method, Short-Time Fourier Transform (STFT) method, Variational Mode Decomposition (VMD) method;

determining phase differences between the components to detect out-of-phase relationships, wherein out-of-phase relationships indicate variability in phase alignment over time; and quantifying the synchrony or asynchrony using a phase synchrony index, wherein the phase synchrony index is a numerical measure of consistency of phase differences, wherein a higher index indicating synchrony and a lower index asynchrony.

13. The method of claim 1, wherein identifying the breathing abnormality comprises:

detecting asynchrony between thoracic, diaphragmatic and abdominal breathing components based on the analysed phase differences;

identifying imbalance in the relative contributions of thoracic, diaphragmatic and abdominal components to the overall breathing effort; and classifying the detected asynchrony and the identified imbalance as the breathing abnormality.

14. The method of claim 1, wherein detecting the potential cardiorespiratory condition comprises:

correlating the identified breathing abnormality with a predefined cardiorespiratory condition; and determining the potential cardiorespiratory condition based on the correlated abnormality.

15. A system for assessing cardiorespiratory health, the system comprising:

a plurality of ballistocardiography (BCG) sensors embedded in a support surface and positioned to correspond to thoracic, diaphragmatic, and abdominal regions of a torso of a subject, the plurality of BCG sensors configured to acquire analog signals representing mechanical forces caused by breathing movements without physical contact with skin of the subject configured to measure mechanical forces caused by breathing movements;

at least one low-noise amplifier and at least one analog-to-digital converter operatively connected to the plurality of BCG sensors and configured to amplify and digitize the analog signals to generate mechanical movement data; and a processor operatively connected to the plurality of BCG sensors, wherein the processor is configured to:

generate mechanical movement data from the measured mechanical forces;

filter the mechanical movement data to extract respiratory signal waveforms and heart signal waveforms;

decompose the respiratory signal waveforms into thoracic, diaphragmatic, and abdominal breathing components based on waveform characteristics and anatomical location corresponding to the plurality of BCG sensors;

analyse phase differences between the thoracic, diaphragmatic, and abdominal breathing components over time to quantify a degree of synchrony or asynchrony;

evaluate relative contributions of thoracic, diaphragmatic, and abdominal breathing components to an overall breathing effort;

identify a breathing abnormality based on the analysed phase differences and the evaluated relative contributions;

detect a potential cardiorespiratory condition based on the identified breathing abnormality; and generating an alert based on the detected potential cardiorespiratory condition.

16. The system of claim 15, wherein the plurality of BCG sensors is arranged in a grid pattern on a support surface with a spacing of 10-15 cm to cover the thoracic, diaphragmatic, and abdominal regions of the torso.

17. The system of claim 15, wherein the processor is configured to employ a machine learning model trained on labelled datasets of breathing patterns to classify normal and abnormal breathing patterns, wherein the machine learning model uses the analysed phase differences and the evaluated relative contributions as input features to identify a breathing abnormality.

18. The system of claim 15, wherein the plurality of BCG sensors is configured to capture observed signals as a mix of contributions from multiple breathing sources, and the processor is configured to apply blind source separation techniques to separate the observed signals into underlying source signals, thereby isolating thoracic, diaphragmatic, and abdominal breathing components.

19. The system of claim 15, wherein the processor is configured to calculate a Breathing Contribution Index (BCI) for each of thoracic, diaphragmatic, or abdominal breathing component, and determine the relative contribution of each component as a percentage of the overall breathing effort to identify a dominant breathing component.

20. The system of claim 15, wherein the processor is configured to:

calculate instantaneous phases of the thoracic, diaphragmatic and abdominal breathing components using at least one of: Fourier Transform method, Hilbert Transform (HT) method, Hilbert-Huang Transform (HHT) method, Synchro-squeezing Transform method, Short-Time Fourier Transform (STFT) method, Variational Mode Decomposition (VMD) method;

determine phase differences to detect out-of-phase relationships; and quantify a degree of synchrony or asynchrony using a phase synchrony index, wherein the phase synchrony index is a numerical measure of consistency of phase differences.

* * * * *